(12) United States Patent
Dutton et al.

(10) Patent No.: US 9,763,509 B1
(45) Date of Patent: Sep. 19, 2017

(54) APPLICATOR FOR PERSONAL CARE

(71) Applicant: AVON PRODUCTS, INC., Suffern, NY (US)

(72) Inventors: Simon Nicholas Dutton, New City, NY (US); John Prizzi, Jr., Wyckoff, NJ (US)

(73) Assignee: Avon Products, Inc., Rye, NY (US)

( * ) Notice: Subject to any disclaimer, the term of this patent is extended or adjusted under 35 U.S.C. 154(b) by 0 days.

(21) Appl. No.: 15/381,709

(22) Filed: Dec. 16, 2016

Related U.S. Application Data

(60) Provisional application No. 62/351,785, filed on Jun. 17, 2016, provisional application No. 62/351,770, filed on Jun. 17, 2016.

(51) Int. Cl.
| | | |
|---|---|---|
| *B43K 5/02* | (2006.01) | |
| *A45D 40/26* | (2006.01) | |
| *A45D 34/04* | (2006.01) | |

(52) U.S. Cl.
CPC .......... *A45D 40/26* (2013.01); *A45D 34/04* (2013.01); *A45D 40/262* (2013.01); *A45D 2200/055* (2013.01); *A45D 2200/056* (2013.01); *A45D 2200/1009* (2013.01)

(58) Field of Classification Search
CPC .......... A45D 34/04; A45D 2200/053; A45D 2200/1009; A45D 2200/1018
USPC ............................................ 401/188 R, 131
See application file for complete search history.

(56) References Cited

U.S. PATENT DOCUMENTS

| | | | | |
|---|---|---|---|---|
| 3,069,718 | A * | 12/1962 | Brady ............... | A45D 34/041 401/218 |
| 4,235,557 | A * | 11/1980 | Hayes ................ | A45D 40/00 401/49 |
| 4,708,267 | A | 11/1987 | Sieverding et al. | |
| 6,511,243 | B2 * | 1/2003 | Miranda ............. | A45D 34/041 401/131 |
| 7,980,777 | B2 * | 7/2011 | Kennedy ............. | B05C 17/002 222/383.1 |
| 8,267,610 | B2 * | 9/2012 | Goodman .......... | B05C 17/002 222/183 |

(Continued)

FOREIGN PATENT DOCUMENTS

| | | |
|---|---|---|
| CN | 301487541 S | 3/2011 |
| CN | 301680497 S | 9/2011 |
| CN | 302046383 S | 8/2012 |

(Continued)

OTHER PUBLICATIONS

Search Report to corresponding Taiwanese Design Patent Application No. 105307680 completed Jun. 3, 2017 (1 page).

(Continued)

*Primary Examiner* — Jennifer C Chiang
(74) *Attorney, Agent, or Firm* — Brian McCloskey; Elizabeth Morters

(57) ABSTRACT

A fragrance product for dispensing and topically applying a viscous fragrance composition, such as a gel, is provided. The product includes an applicator which may house a charge of fragrance composition and which may comprise a hemispherical head portion for spreading a film of the fragrance composition onto a human integument. The product further includes a base for seating and storing the applicator. Methods of using the fragrance product are also described.

12 Claims, 11 Drawing Sheets

(56) References Cited

U.S. PATENT DOCUMENTS 8,821,059 B2 * 9/2014 Sasaki .................... A45D 33/02
                                                                401/132
9,440,056 B2 * 9/2016 Hofland .............. A61M 35/003

FOREIGN PATENT DOCUMENTS

| FR | 2492241 A1 | 4/1982 |
|----|------------|--------|
| WO | 0119215 A1 | 3/2001 |
| WO | 2005025523 A2 | 3/2005 |

OTHER PUBLICATIONS

International Search Report and Written Opinion to corresponding International Application No. PCT/US2017/035368 dated Jul. 25, 2017 (12 pages).

* cited by examiner

APPLICATOR FOR PERSONAL CARE

RELATED APPLICATIONS

This application claims the benefit under 35 U.S.C. 119(e) to U.S. Provisional Application Ser. No. 62/351,785, filed Jun. 17, 2016, and U.S. Provisional Application Ser. No. 62/351,770, filed Jun. 17, 2016, the entirety of which are hereby incorporated by reference herein for all purposes.

FIELD OF INVENTION

A product for dispensing and topically applying a viscous composition, such as a gel, is provided. The product includes an applicator which may house a charge of composition and which may comprise a hemispherical head portion for spreading a film of the composition onto a human integument. The product further includes a base for seating and storing the applicator. Methods of using the product are also described.

BACKGROUND

Traditionally, cosmetic products in the fragrance category are provided in the form of ethanolic solutions or essential oils which are sprayed or dabbed onto the skin. Recently, a gel-based fragrance composition has been described in U.S. Patent Publication No. 2015/0208647, the entire contents of which are hereby incorporated by reference. While such gel-based fragrances have many advantages, including the ability to deliver prolonged fragrance release, they may be difficult to spray due to their high viscosity and therefore might not be ideally suited for conventional fragrance packaging. The highly viscous or thixotropic nature of some fragrance gels also may cause the material to adhere to the inner walls of the container and thus be unavailable for pumping or otherwise inaccessible to the consumer. This phenomenon is known as "coring," and results from the central portion of the charge of fragrance composition being preferentially expelled by a pump, leaving a ring of material on the walls of the reservoir. Coring is particularly problematic with highly viscous gels which lack the bulk flow properties to readily redistribute within the container. A specialized applicator adapted to deliver fragrance gels and other viscous compositions would therefore be desirable.

It is therefore an object of the invention to provide a fragrance product adapted to store and/or deliver viscous compositions, such as fragrance gels.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In accordance with one or more of the foregoing objectives and others, the present invention provides a fragrance product that includes an applicator suitable for applying a wide variety of cosmetic and personal care compositions to the user's skin. The product typically comprises an applicator for applying compositions and base portion for storage of the applicator when not in use. In some implementations, the applicator may be generally mushroom shaped, comprising a handle and a bulbous head portion adapted to spread a thin film of a composition onto a human integument (e.g. skin, etc.). In some embodiments of the invention, the product may comprise:

(i) an applicator having a handle and a bulbous (e.g., substantially hemispherical, substantially hemiovoidal, etc.) head portion with an outer surface adapted to spread a liquid composition onto human skin; and (ii) a base portion which may comprise on its top side a recess geometrically matching the outer surface of the head portion such that the applicator may be seated on the base by positioning the head portion of the applicator within the recess.

The applicator may comprise a chamber in its interior and contain a charge of composition (e.g., a fragrance composition, skin care composition, sunscreen, etc.) within the chamber. In the following description, references made to fragrance compositions and applicators therefor, although it will be understood that the applicators and methods of the invention are equally applicable to any flowable composition including skin care compositions, hair care compositions, sunscreen compositions, color cosmetics and the like. In some implementations, the applicator is capable of dispensing a portion of the fragrance composition, for example, through an exit orifice located on the head portion, optionally using a pump (e.g, atmospheric, airless, etc.) which also may be disposed within the chamber. The applicator typically has a handle configured to be gripped by a user to remove the applicator from the base and manipulate the applicator during application of the fragrance composition to the skin. The handle may be integral with the head portion, for example, joined together by a snap fit, weld, or the like, or may be separable such that the handle and head are moveable with respect to one another. The applicator head generally has a large surface area (e.g., up to about 200 cm$^2$) to help spread the fragrance composition onto a human integument. In some embodiments, the chamber is formed at least partially within the head portion of the applicator but may also extend into the handle portion. In some embodiments, a major portion of the fragrance composition is contained within the head portion. In other embodiments, at least 60%, or at least 70%, or at least 80%, or at least 90% of the volume of the composition is contained within the head portion. In one implementation, substantially all of the composition is contained within the head portion. The applicator may comprise a pump mechanism to facilitate expulsion of the fragrance composition from the chamber through an outlet orifice to the exterior of the applicator. The outlet orifice may be positioned at any location on the head portion but is typically at the terminal end of the head portion, e.g., along the axis through the applicator head and handle. An actuator, such as a button on the handle, may be included to control the pump.

In some embodiments, the applicator is symmetric about a common axis through the handle portion and the head portion (the primary axis of the applicator) and may be axisymmetrical with respect to the primary axis. The head portion may take any shape and be composed of any material useful for spreading a fragrance composition. In some embodiments, the outer surface of the head portion is substantially hemispherical. In some embodiments, the head portion has a smooth surface, and may be composed of metal, plastic or glass. Typically the head portion has a large surface area to help facilitate the application of fragrance composition into a thin film. In some embodiments, the outer surface of the head portion has a surface area of from about 2 cm$^2$ to about 200 cm$^2$ (e.g., about 3-100 cm$^2$, about 5-50 cm², or about 10-30 cm²). In one embodiment, the outer hemispherical surface of the head portion may have a surface of about 20-30 cm².

Typically, the fragrance composition is expelled from the chamber within the applicator through the outlet orifice upon actuation of a pump mechanism. In some embodiments, the outlet orifice is surrounded by a sensorial element, which may be a different material than that of the surface of the head. This sensorial element provides a feeling on the skin that is different from the surface of the head portion. This different sensorial feeling may be any sensorial feeling to help a user locate the approximate position of the outlet orifice on their skin (e.g., temperature differential, texture, etc.). For example, the sensorial element may be ceramic, metallic or flocked. In some embodiments, the sensorial element is an annular ring or disc with an orifice positioned directly coincident with the orifice in the head.

In various embodiments, the applicator comprises a chamber which may be located at any position within or on the applicator. In some embodiments, the chamber may be formed, at least partially, within the head portion of the applicator. The flowable composition may be disposed within the chamber. In some embodiments, the volume of the chamber may range from about 5 mL to about 100 mL (e.g., 10 to about 50 mL, etc.) and may contain anywhere from 0.1-100 mL or from 1-50 mL or from 10-30 mL of composition. In some embodiments, the chamber further comprises a pump mechanism in order to help expel the flowable composition contained within the chamber through the orifice to the exterior of the applicator. In some embodiments, the fragrance composition may be contained within a flexible, collapsible bag, which is positioned within the chamber. In some embodiments, the collapsible bag is airless. A pump mechanism may be attached to the bag, for example, by sonic welding to create an air-tight seal between the interior of the bag and the inlet side of the pump. Actuation of the applicator by a user causes a portion of the fragrance composition, in contact with the inlet side of the pump to be expelled through the pump and out of the orifice, with a concomitant decrease in the volume of the bag. The bag may be composed of a multilaminate material, such as aluminum foil, polyethylene, or combinations thereof.

The fragrance product of the invention also comprises a base portion in order to seat and/or store the applicator when not in use and/or to close off the orifice when the applicator is not in use. Typically, the base portion has a recess that is geometrically matched with a portion of the applicator. In some embodiments, the base portion may comprise a recess which geometrically matches the head portion of the applicator. This geometrical matching allows the applicator to be seated on the base by positioning of the head portion within the recess. In some embodiments a protrusion may be provided on the surface of the recess to engage the outlet orifice when the applicator is seated on the base. The engagement of the protrusion and the outlet orifice may substantially seal the outlet orifice and help align and stabilize the applicator within the base.

When the applicator is seated in the base, the base may serve to keep the applicator in a specific orientation with respect to the surface plane upon which the base sits. In some embodiments, the applicator and the base together form a substantially continuous outer contour when the applicator is seated on the base. The applicator is typically seated such that the outlet orifice faces downward and the handle portion faces upward, such that the flowable composition may settle over time near the outlet orifice while permitting the handle to be easily gripped by the user to remove the applicator from the base. For example, the applicator may be positioned on the base such that the outlet orifice is located at the deepest point of the recess. In some embodiments, the primary axis of the applicator and the surface plane are either normal or parallel when the applicator is seated in the base.

In some embodiments of the invention, the fragrance product may comprise:
  (i) an axisymmetric applicator having a handle portion and a head portion having an outer surface adapted to spread a fragrance composition onto human skin, and a chamber formed at least partially within the head portion for holding a charge of the fragrance composition, a pump disposed at least partially within the chamber capable of expelling the fragrance composition through an outlet orifice in the head portion upon actuation, and an actuator adapted to permit the user to actuate the pump mechanism, and optionally a sensorial element proximate (e.g., surrounding) the orifice; and
  (ii) a base portion having a top and a bottom, the base comprising on its top side a recess configured to geometrically match at least a portion of, or substantially all of, the outer surface of the head portion, such that the applicator may be seated on the base by positioning the head portion of the applicator within the recess, the base further including a protrusion extending from the surface of the recess for engaging said orifice.

The pump mechanism may include any mechanism that exerts a force on a flowable material contained in the applicator to expel the flowable material through the outlet orifice. The pump mechanism may be, for example, atmospheric or airless. In some embodiments, the pump mechanism includes at least one one-way valve, and is in fluid communication with the chamber of the applicator and with the outlet orifice. In some embodiments, the pump mechanism comprises an elastic membrane which may be actuated to expand to reduce the volume within and thereby cause the expulsion of the fragrance composition through the outlet orifice. The actuation of the elastic membrane may be, for example, impingement of a physical element (e.g., a rod, post, plunger, piston, etc.) onto the membrane to cause displacement, or actuated by increasing the pressure of air on one side of the membrane. In other embodiments, the pump mechanism may comprise multiple chambers designed to control the flow of the composition between each chamber. In some embodiments, control of flow is achieved through mechanisms on each chamber designed to allow passage between chambers at certain points during actuation. In other embodiments, control of the flow may be achieved by one-way valves situated between chambers. The pump mechanism may consist of as many one-way valves as necessary for the pump mechanism to work. For example, the pump mechanism may consist of zero, one, two, three, four five, ten, etc. one-way valves.

The pump mechanism may be actuated by an actuator located at any position on the applicator. Typically, a user will actuate the pump mechanism by applying an actuating force to the pump actuator. In some embodiments, the handle of the applicator may comprise the actuator. The actuator may be, for example, a button on the handle. In other embodiments, actuation of the pump mechanism may occur via movement of certain portions of the applicator with respect to one another. For example, in some embodiments, the applicator may be configured to actuate the pump by movement of head portion with respect to handle. The head portion and the handle portion may be separate pieces capable of undergoing a movement that brings them closer to one another than when in an unperturbed position (i.e. the position no actuating force has been applied to the applicator) to actuate the pump. The applicator may further comprise a spring mechanism bias motion of the head relative to the handle and to return the applicator to the unperturbed position once the actuating force is removed.

Any flowable fragrance composition can be used in the applicator. In some embodiments, the fragrance composition is a liquid. As used herein, the term "liquid," includes any condensed phase that has a measurable viscosity (e.g., 5,000 cps-1,500,000 cps) at 10 s$^{-1}$ (25° C.), and includes gels. The liquid fragrance composition may be, for example, in the form of an ointment, cream, lotion, liquid-phase, gel, emulsion, emulsified gel, mousse or foam. In some embodiments, the fragrance composition is a fragrance gel. It is believed that the fragrance gel compositions described in U.S. Patent Publication No. 2015/0208647, the disclosure of which is incorporated by reference in its entirety, will be particularly useful.

Although the preferred composition for use with the fragrance product is a fragrance product, any cosmetic product can be used in the applicator. For example, the cosmetic product may be a skin care product, a sunscreen product, or a hair care product.

The base is transparent or translucent. In some embodiments, the head portion, including the substantially hemispherical surface is visible through the transparent base portion when the applicator is docked on the base.

In some embodiments, the fragrance composition is highly viscous, and may have a viscosity from about 1,000 cps to about 1,500,000 cps (for example, between about 5,000 cps and about 1,000,000 cps, or between about 10,000 cps and about 500,000 cps, etc). Unless otherwise indicated, viscosity is measured at 25° C. with a shear rate of 10 s$^{-1}$.

Advantageously, the applicator of the invention may ameliorate problems, such as coring, associated with highly viscous compositions. In some implementations, the applicator is capable of expelling at least 75%, by weight of the initial charge of the chamber over the useful lifetime of the product. In some embodiments, at least about 80% by weight (e.g. at least about 90% by weight, at least about 95% by weight) of the initial charge of fragrance composition (i.e., prior to first use) contained within the chamber can be expelled from the applicator over the useful lifetime of the product. As used herein, percentage of fragrance composition that can be expelled from the applicator is the amount of fragrance composition that is expelled relative to the initial charge of composition (i.e., the original "full" amount before the first use), from repeated actuations until successive actuation no longer expels any fragrance composition.

In another aspect, the present invention provides methods of applying a fragrance product to an integument comprising:
  (a) providing a fragrance product as described herein, for example, having an applicator and a base, wherein the applicator comprises a handle and a head portion with a substantially hemispherical smooth outer surface;
  (b) removing the applicator from the base;
  (c) actuating a pump within the applicator to release a portion of a charge of fragrance composition from within a chamber in the applicator out through an orifice to the exterior of the applicator;
  (d) spreading the composition onto a human integument by rolling or rubbing the substantially hemispherical smooth outer surface of the head portion against the aliquot of fragrance composition to form a film of said fragrance composition on said integumentary surface; and
  (e) optionally seating the applicator on the base after use.

These and other aspects of the present invention will become apparent to those skilled in the art after a reading of the following detailed description of the invention, including the appended claims.

BRIEF DESCRIPTION OF THE DRAWINGS

FIG. 1A is a top view of the embodiment. FIG. 1B is a side view of the embodiment and FIG. 1C is a perspective view of the embodiment.

DETAILED DESCRIPTION OF THE INVENTION

Detailed embodiments of the present invention are disclosed herein; it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to employ the present invention.

Figure 1A:
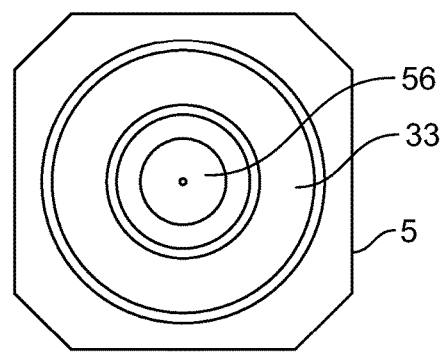
FIGS. 1A-1C depict three views of an embodiment of the present invention where the applicator is seated in the base.
Figure 1B:
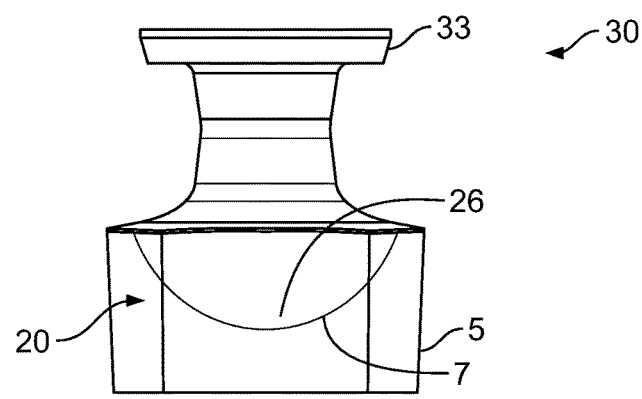
Figure 1C:
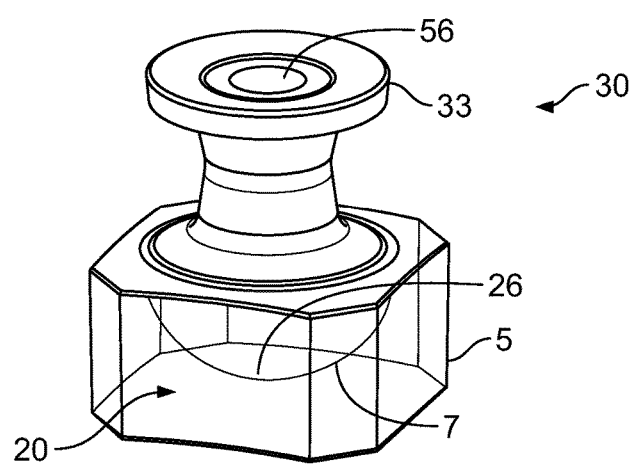

In some embodiments of the invention, the fragrance product comprises an applicator that can be seated and/or stored in a base. Referring to FIGS. 1A-1C, a fragrance product comprises an applicator seated in a base 5. The applicator comprises a head portion 20 with a substantially hemispherical outer surface 26 and a handle portion 30. The handle portion comprises an annular or discoid feature 33 to allow the user to grip the applicator to remove the applicator from the base 5, and to hold the applicator during use. Base 5 has a recess 7 on its top side that is geometrically matched with outer surface 26 of the head portion 20 so that the applicator can be snuggly mounted on the base. The applicator has a button actuator 56 on handle portion 30 upon which can actuate an internal pump mechanism and dispel a flowable composition contained within the applicator.

Figure 2:
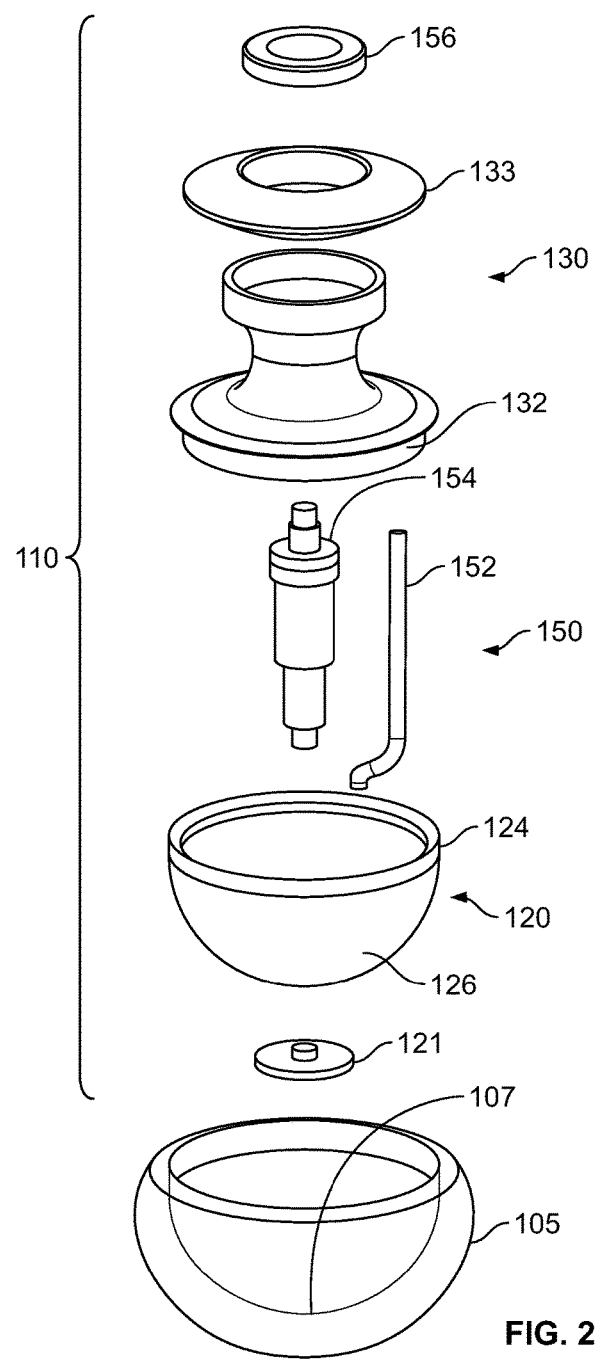
FIG. 2 is an exploded view of another embodiment of the invention.
Figure 3:
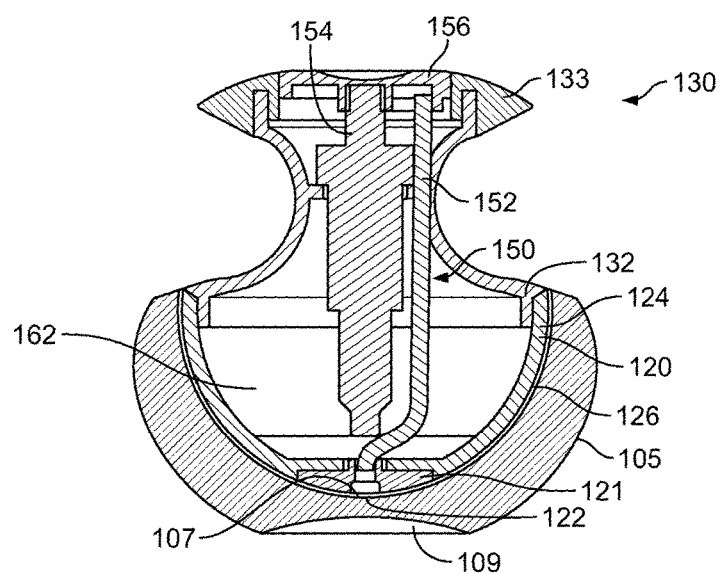
FIG. 3 is a cross sectional side view of an embodiment of the applicator shown in FIG. 2.

Referring to FIGS. 2 and 3, an applicator 110 with a head 120 geometrically matched to recess 107 in base 105 is depicted. The applicator 110 comprises head portion 120, handle portion 130, and a pump mechanism 150. The head portion has an outer surface 126 geometrically matched with recess 107 in the base portion 105. The head portion further comprises a sensorial element 121 which may be composed of a different material than the outer surface 126 of the head portion 120. The head portion has a ring 124 that allows head portion 120 to be mated (e.g. press fit) with sleeve 132. The handle portion comprises an annular feature 133 to allow a user to grip the applicator that accommodates a button actuator 156. Atmospheric pump mechanism 150 comprises a pump 154 and a return tube 152. Pump mechanism 150 is actuated by the actuator button 156. Depressing the actuator button 156 causes the composition contained within return tube 152 to be expelled out the outlet orifice 122. As the actuator returns to the original position, the composition contained within the chamber 162 is transported through the pump mechanism 154 towards the entrance of return tube 152. Ultimately, the return tube 152 is refilled with the flowable composition. Return tube 152 is mated with the outlet orifice 122 and the sensorial element 121 to allow expulsion of the flowable composition. Additionally, base 105 has a flat or planar bottom 109 in order for the base to be stable on a surface plane.

Figure 4:
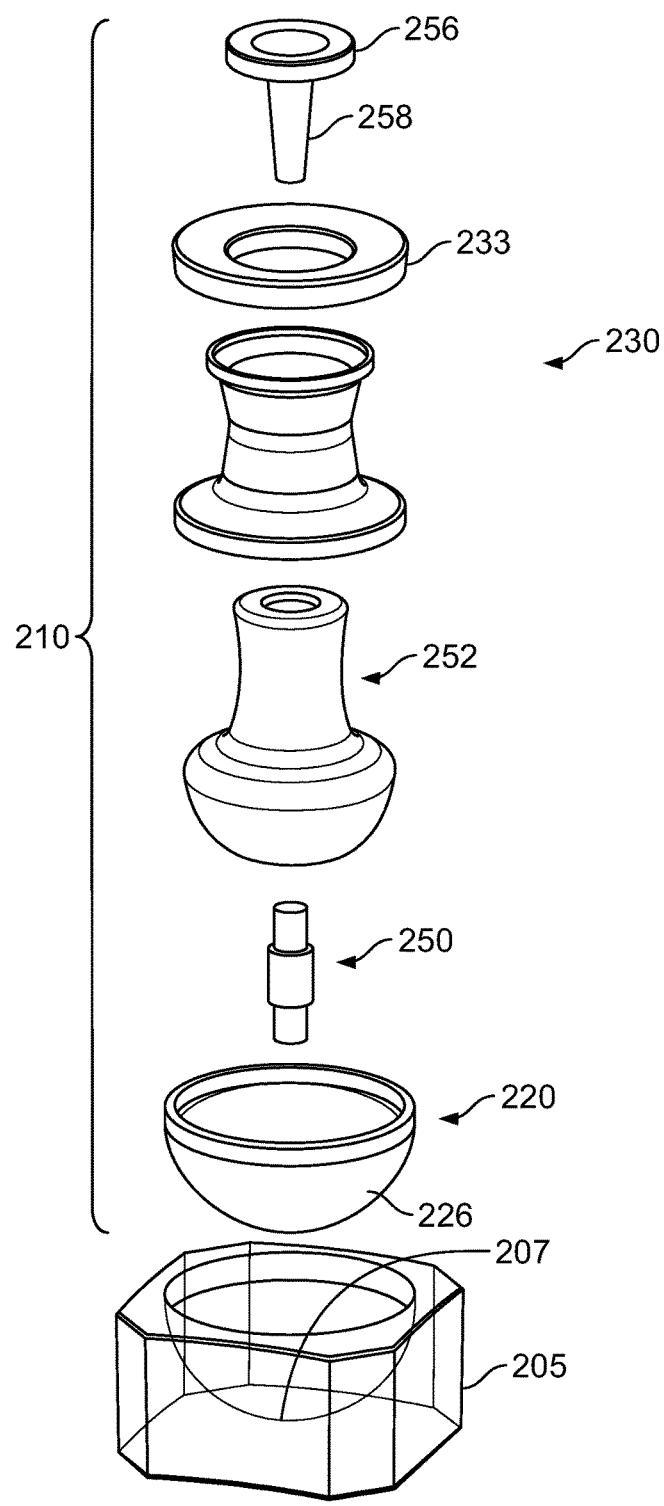
FIG. 4 is an exploded view of another embodiment of the invention.
Figures 5, 6:
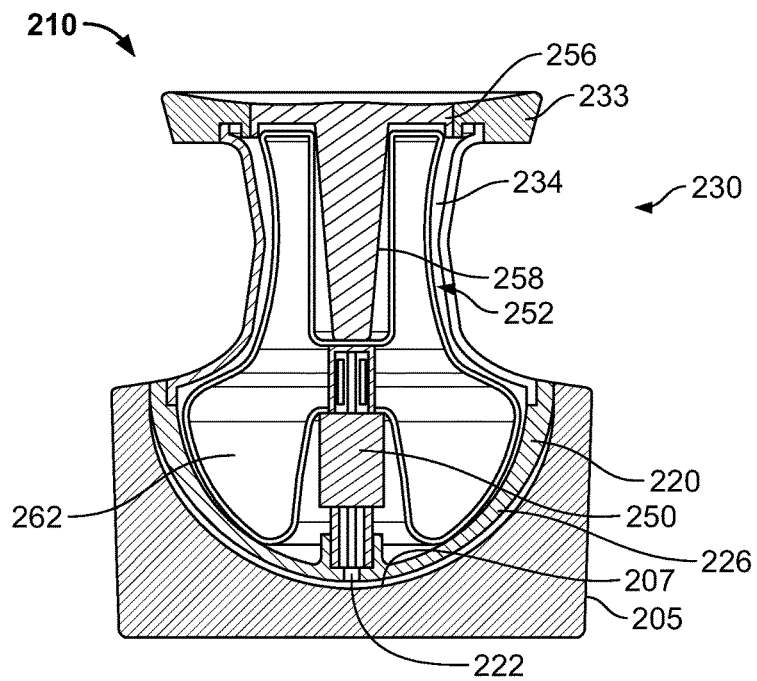
FIG. 5 is a cross sectional side view of the embodiment depicted in FIG. 4.
FIG. 6 is a cross sectional side view of another embodiment.

Referring to FIGS. 4 and 5 an applicator 210 and base 205 are shown. The applicator comprises a head portion 220, handle portion 230, and pump mechanism 250. The outer surface of the head portion 220 is geometrically matched with recess 207 in base 205. The handle portion comprises an annular feature 233 to allow a user to grip the applicator. Within annular feature 233 is a button actuator 256 that comprises a substantially cylindrical portion 258 extending into chamber 234 to engage pump 250. A collapsible bag 252 filled with cosmetic composition surrounds cylindrical portion 258 and pump mechanism 250. Collapsible bag 252 is sealed such that air is substantially unable to flow into or out of its interior volume 262. The bag is sealed to the inlet of pump 250 so that inlet is in fluid communication with the composition within the bag. The pump 250 is in communication with the outlet orifice 222. Interior volume 262 may contain a composition. Actuation of the pump mechanism causes the composition to be expelled through orifice 222 thereby decreasing the interior volume 228 of bag 262.

Referring to FIG. 6, an applicator 310 seated in base 305 is depicted. Actuation of button actuator 356 causes movement of expandable piston 354 downward into chamber 362 in the non-linear column 352. Movement of expandable piston 354 forces a flowable composition contained in chamber 356 into contact with pump mechanism 350 which expels the flowable composition out of outlet orifice 322.

Figure 7:
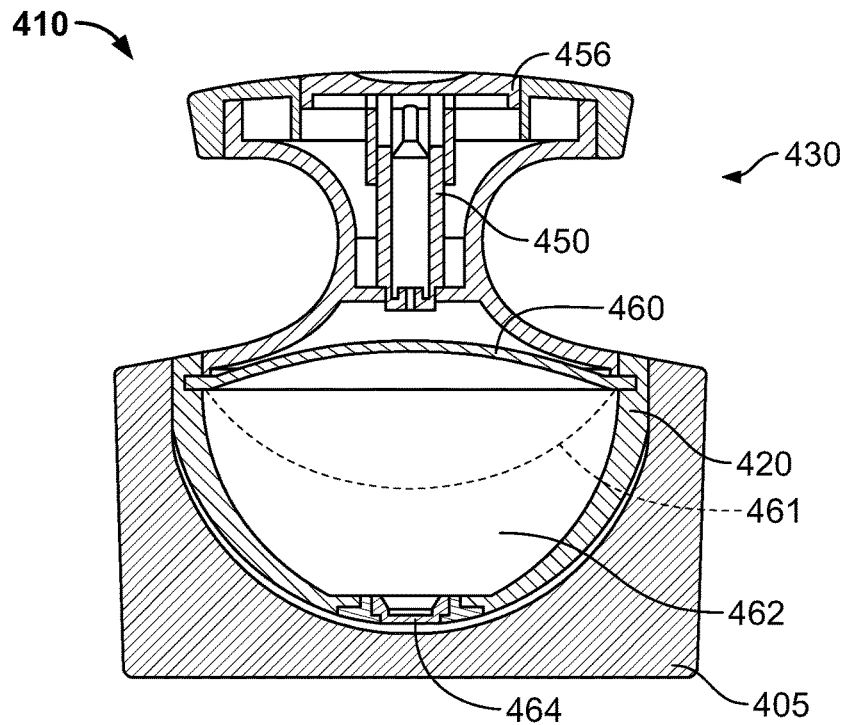
FIG. 7 is a cross sectional side view of another embodiment.

Referring to FIG. 7, an applicator 410 seated in base 405 is depicted. Actuation of button actuator 456 actuates pump mechanism 450 which exerts a force on an elastic membrane 460. This force causes the elastic membrane to expand and move to, for example, position 461. This movement decreases the volume in chamber 462 thereby resulting in the expulsion of a composition contained in chamber 462 out of orifice 464 in head portion 420.

Figure 8:
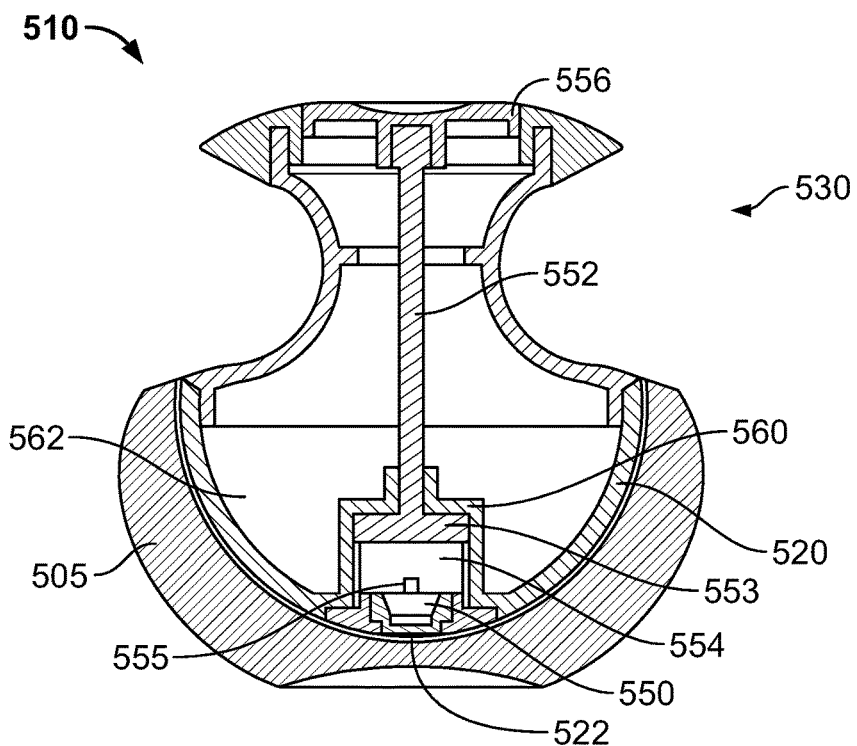
FIG. 8 is a cross sectional side view of another embodiment.

Referring to FIG. 8, an applicator 510 seated in base 505 is depicted. A composition is contained in chamber 562. Chamber 554 is part of the pump mechanism and is separated from chamber 562 by wall 560 that may have one or more apertures 555 to permit a composition in chamber 562 to flow into and fill chamber 554. Wall 560 is adapted allow plunger 553 and piston 552 entry into chamber 554 such that movement of actuator 556 translates to movement of piston 552 and plunger 553 in chamber 554. If actuator 556 is depressed, plunger 553 decreases the volume in chamber 554 thereby expelling the composition through pump mechanism 550 and out orifice 522 on head portion 520. As plunger 553 returns to its original position, the volume in chamber 554 increases thereby causing composition in chamber 562 to flow through aperture 555 and fill chamber 554. Aperture 555 may comprise a one-way valve.

Figure 9:
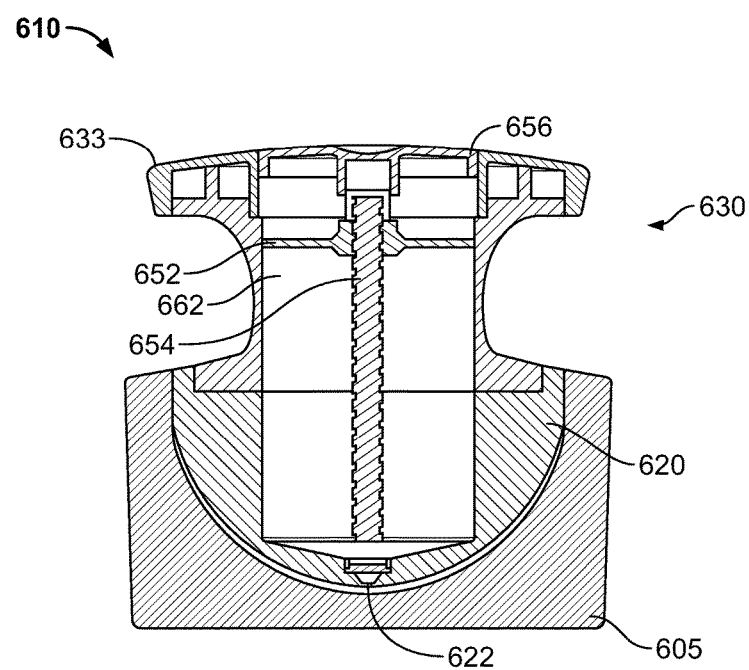
FIG. 9 is a cross sectional side view of another embodiment.
Figure 10A:
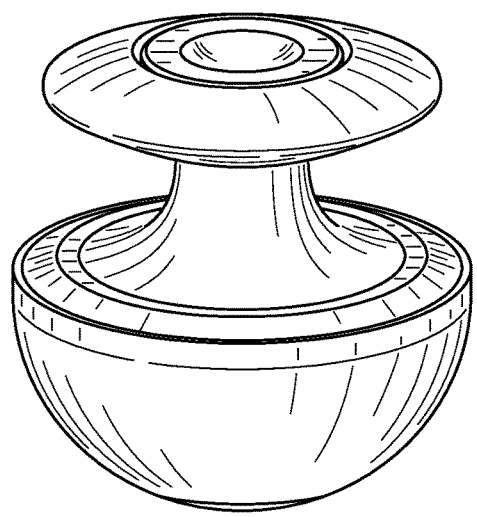
FIG. 10A illustrates an embodiment of the applicator of the invention comprising a flange shaped handle portion connected to a hemispherical head portion by a neck. The handle portion comprises a button actuator and the head has a sensorial element at its terminal end.
Figure 10B:
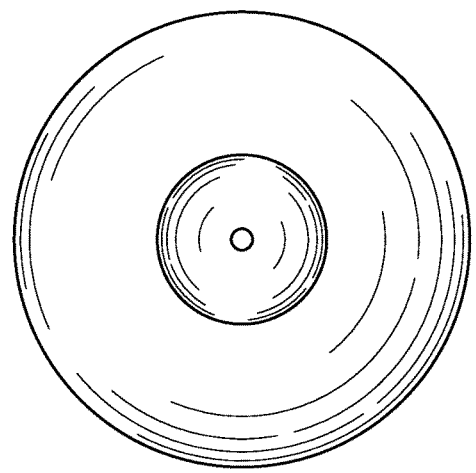
FIG. 10B illustrates a view of the bottom of the embodiment shown in FIG. 10A looking from the bottom along a central axis through the head and handle, showing the sensorial element and the orifice at the central axis where the sensorial element surrounds the exit orifice.
Figure 11:
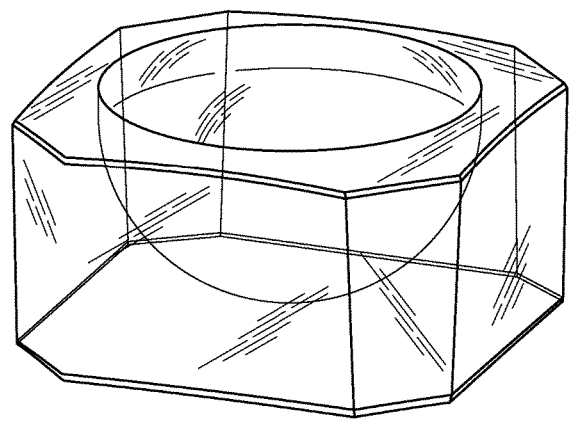
FIG. 11 is a perspective view of a base for the applicator of FIG. 10A, formed from a transparent or translucent material, with a hemispherical recess that is geometrically matched to complement the hemispherical head portion of the applicator of FIG. 10A.
Figure 12:
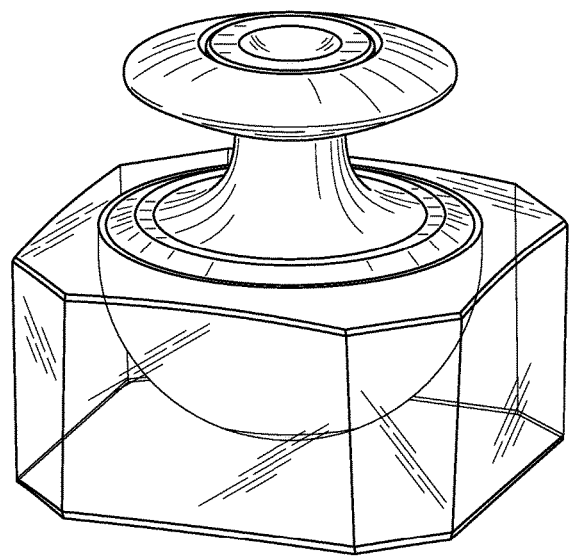
FIG. 12 illustrates the applicator of FIG. 10A seated in the base of FIG. 11.
Figure 13:
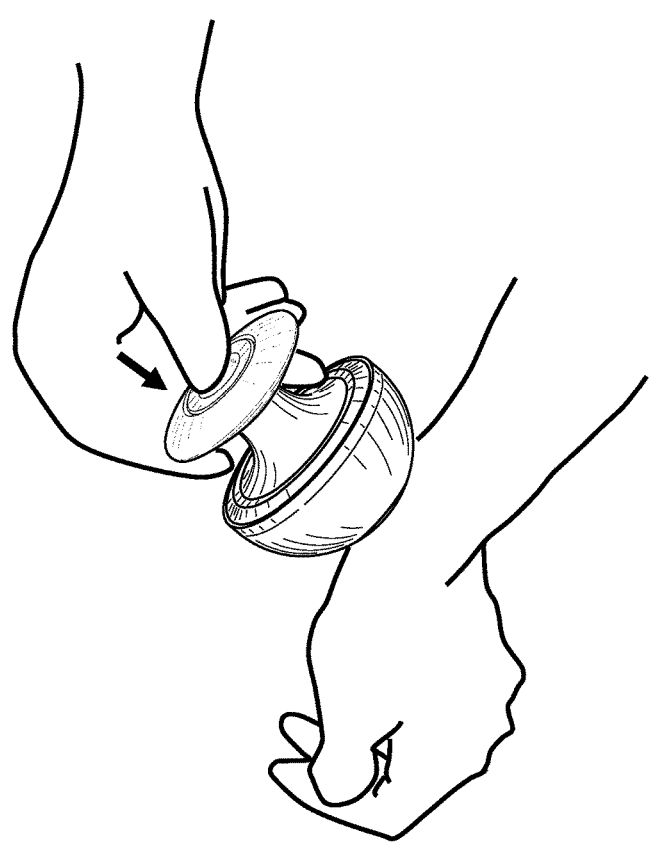
FIG. 13 illustrates the applicator of FIG. 10A in use, wherein a user grips the applicator with fingers beneath the flange of the handle portion and actuates the button actuator with the thumb (illustrated by the arrow). The sensorial element and exit orifice of the head portion are contacted with skin where a cosmetic product contained within the applicator will be applied and spread over the skin with the hemispherical head portion.

Referring to FIG. 9, applicator 610 is seated in base 605. The applicator comprises head portion 620, handle portion 630 and a chamber 662. The applicator has a screw-type dispenser of the type commonly used with lip stick, anti-perspirants, etc., whereby turning the screw using an actuator (e.g., a turnable wheel), advances a dam which restricts its volume of the the chamber, causing the composition to be expelled through an orifice. The volume of chamber 662 is defined by the interior of head portion 620, handle portion 630, and ceiling 652. The handle portion comprises an extended gripping portion 633 and actuator 656 that is coupled to threaded column 654. Rotation of actuator 656, which occurs via the rotation of handle portion 630 with respect to head portion 620 causes downward movement of ceiling 652 via threaded column 654, thereby reducing the volume of chamber 662 and expelling any composition contained therein through outlet orifice 622 located on the outer surface of head portion 620.

In some embodiments, the handle comprises a radial flange. In some embodiments, the flange is radially symmetric. In other embodiments, the flange is radially asymmetric, such that portions of the lip may extend to a position above the top surface of the button actuator and other portions of the lip may extend to a position below the top surface of the button actuator.

In some embodiments, the applicator may comprise an internal wall underneath the wall connecting the head portion to the handle portion. The internal wall may define an internal volume connected to a chamber. The applicator may comprise a chamber in fluid contact with the pump mechanism. Actuation of the button actuator may cause the structure defined by the internal wall to move downward with respect to the external wall. This movement may actuate the pump mechanism. This movement is similar to the movement of a syringe although the operational mechanics of the pump mechanism may or may not be similar. Actuation of this pump mechanism may cause the expulsion of the composition to the exterior of applicator through outlet orifice. In some embodiments, the button and structure defined by the inner wall return to their original position following actuation, for example, by action of a spring mechanism. In other embodiments, the button and structure defined by wall do not return to their original position following actuation. In some embodiments, the chamber may further comprise a collapsible bag containing a flowable composition. The collapsible bag may be sealed such that air is substantially unable to flow into or out of its interior volume. The bag is sealed to the inlet of pump mechanism so that the inlet is in fluid communication with the composition within the bag. Actuation of the pump mechanism may cause the composition to be expelled through orifice while no air is transferred into the collapsible bag, thereby decreasing the interior volume of the bag.

The invention claimed is:

1. A product for personal use comprising:
    an applicator comprising a substantially hemispherical head portion having a smooth outer surface adapted to spread a liquid composition onto human skin, the head portion being connected to a handle configured to be gripped by a user; the applicator comprising a chamber formed at least partially within said head portion for holding a charge of a composition; the applicator further comprising a pump disposed at least partially within said chamber for dispensing said composition through an outlet orifice defined in said head portion; wherein said handle comprises an actuator for actuating said pump; and
    wherein the composition is a fragrance gel having a viscosity between about 5,000 cps and about 1,000,000 cps measured at 25° C. with a shear rate of 10 s$^{-1}$, wherein said fragrance gel comprises one or more fragrance oils.

2. The product according to claim 1, further comprising a base portion comprising a recess geometrically matching said head portion of said applicator such that said applicator may be seated on said base by positioning said head portion with said recess.

3. The product according to claim 2, wherein said base portion further comprises a protrusion on the surface of said recess configured to engage said orifice when said applicator is seated in said base.

4. The product according to claim 1, wherein said applicator is symmetric about a common axis through said handle and said head portion.

5. The product according to claim 4, wherein said orifice is located on said axis.

6. The product of claim 1 further comprising a sensorial element surrounding said orifice on the exterior of said outer surface of said head portion; wherein said sensorial element provides a sensorial feeling different from said outer surface of said head portion.

7. The product of claim 6 wherein said sensorial element is ceramic, metallic or flocked.

8. The product of claim 1 wherein said chamber has a volume of from about 10 to about 100 mL.

9. The product of claim 1 wherein said chamber contains from about 10 mL to about 35 mL of said composition.

10. The product of claim 1, wherein said smooth outer surface of said substantially hemispheric head portion has a surface area of from about 2.5 cm$^2$ to about 365 cm$^2$.

11. The product of claim 1, wherein said smooth outer surface of said substantially hemispheric head portion has a surface area of from about 10 cm$^2$ to about 95 cm$^2$.

12. The product of claim 3, wherein said orifice is facing downward and said handle is facing upward when said applicator is seated in said base.

* * * * *